United States Patent
Odanaka et al.

[11] Patent Number: 5,830,126
[45] Date of Patent: Nov. 3, 1998

[54] ENDOSCOPE UNIT

[75] Inventors: Kunio Odanaka; Kunihiko Miyagi, both of Tokyo, Japan

[73] Assignee: Machida Endoscope Co., Ltd., Tokyo, Japan

[21] Appl. No.: 867,409

[22] Filed: Jun. 2, 1997

[30] Foreign Application Priority Data

Jun. 14, 1996 [JP] Japan .................................. 8-175988

[51] Int. Cl.$^6$ ...................................................... A61B 1/12
[52] U.S. Cl. .......................... 600/156; 600/153; 600/158; 600/121; 600/123
[58] Field of Search ................................... 600/121, 122, 600/123, 124, 125, 153, 156, 157, 158, 159

[56] References Cited

U.S. PATENT DOCUMENTS

| | | | |
|---|---|---|---|
| 3,720,203 | 3/1973 | Brown | 600/156 X |
| 4,132,227 | 1/1979 | Ibe . | |
| 5,025,778 | 6/1991 | Silverstein et al. | 600/123 X |
| 5,217,001 | 6/1993 | Nakao et al. | 600/123 |
| 5,353,783 | 10/1994 | Nakao et al. | 600/156 X |
| 5,503,616 | 4/1996 | Jones | 600/123 X |

FOREIGN PATENT DOCUMENTS

| | | |
|---|---|---|
| 19520277 | 2/1995 | Germany . |
| 548462 | 5/1942 | United Kingdom . |
| WO 95/02988 | 2/1995 | WIPO . |

OTHER PUBLICATIONS

European Search Report dated Oct. 16, 1997.

*Primary Examiner*—Beverly M. Flanagan
*Attorney, Agent, or Firm*—Fish & Richardson P.C.

[57] ABSTRACT

An endoscope unit includes an endoscope having an insertion portion and a fluid supply instrument mounted on the insertion portion. The fluid supply instrument comprises a thin resilient tube. This resilient tube is intimately attached to an outer periphery of the insertion portion of the endoscope and radially expansible. A supply member is connected to a basal end of the resilient tube. When fluid from this supply member is supplied to the basal end of the resilient tube, the resilient tube is radially expanded and a fluid passage is formed between the resilient tube and the insertion portion of the endoscope. The fluid is discharged from a distal end of the resilient tube.

5 Claims, 4 Drawing Sheets

ENDOSCOPE UNIT

BACKGROUND OF THE INVENTION

This invention relates to an endoscope unit used for observing or operating ventricles of the brain, etc.

In a surgical operation of the brain, for example, as shown in FIG. 6, a hole X is opened in the skull of a patient, and a guide tube 105 is inserted into this hole X. Then a flexible insertion portion 101 of an endoscope 100 is inserted into this guide tube 105, so that a distal end of the insertion portion 101 is positioned in a brain ventricle A. In that state, the surgeon carries out an operation while observing a diseased part of the brain through the endoscope 100. In order to facilitate a clear observation, it was customarily performed that artificial cerebral spinal fluid (fluid) is charged from a basal end of a channel 102 formed inside the endoscope 100 and this artificial cerebral spinal fluid is supplied into the ventricle from a distal end opening of the channel 102. Then, the artificial cerebral spinal fluid in the ventricle is caused to pass through a gap formed between the insertion portion 101 of the endoscope 100 and the guide tube 105 so as to be discharged from a basal end of the guide tube 105.

Since the flow sectional area of the channel 102 is small in the above conventional endoscope unit, a sufficient quantity of artificial cerebral spinal fluid cannot be supplied. This is especially true when the brain operation is undergoing with forceps inserted into this channel 102 because the flow sectional area of the channel 102 is further reduced. As a consequence, shortage of the supply of artificial cerebral spinal fluid occurs and a clear observation through the endoscope is difficult to obtain.

Such problems are common when fluid is supplied during observation and operation of other parts than the brain ventricles through the endoscope.

SUMMARY OF THE INVENTION

It is, therefore, an object of the present invention to provide an endoscope unit capable of supplying a sufficient quantity of fluid.

According to the present invention, there is essentially provided an endoscope unit including an endoscope having an elongated insertion portion and a fluid supply instrument mounted on the insertion portion of the endoscope, the fluid supply instrument comprising:

(a) a radially expansible thin resilient tube intimately attached to an outer periphery of the insertion portion of the endoscope; and (b) a supply member connected to a basal end of the resilient tube and for supplying fluid to between the resilient tube and the insertion portion of the endoscope.

DETAILED DESCRIPTION OF THE EMBODIMENT

Figure 1:
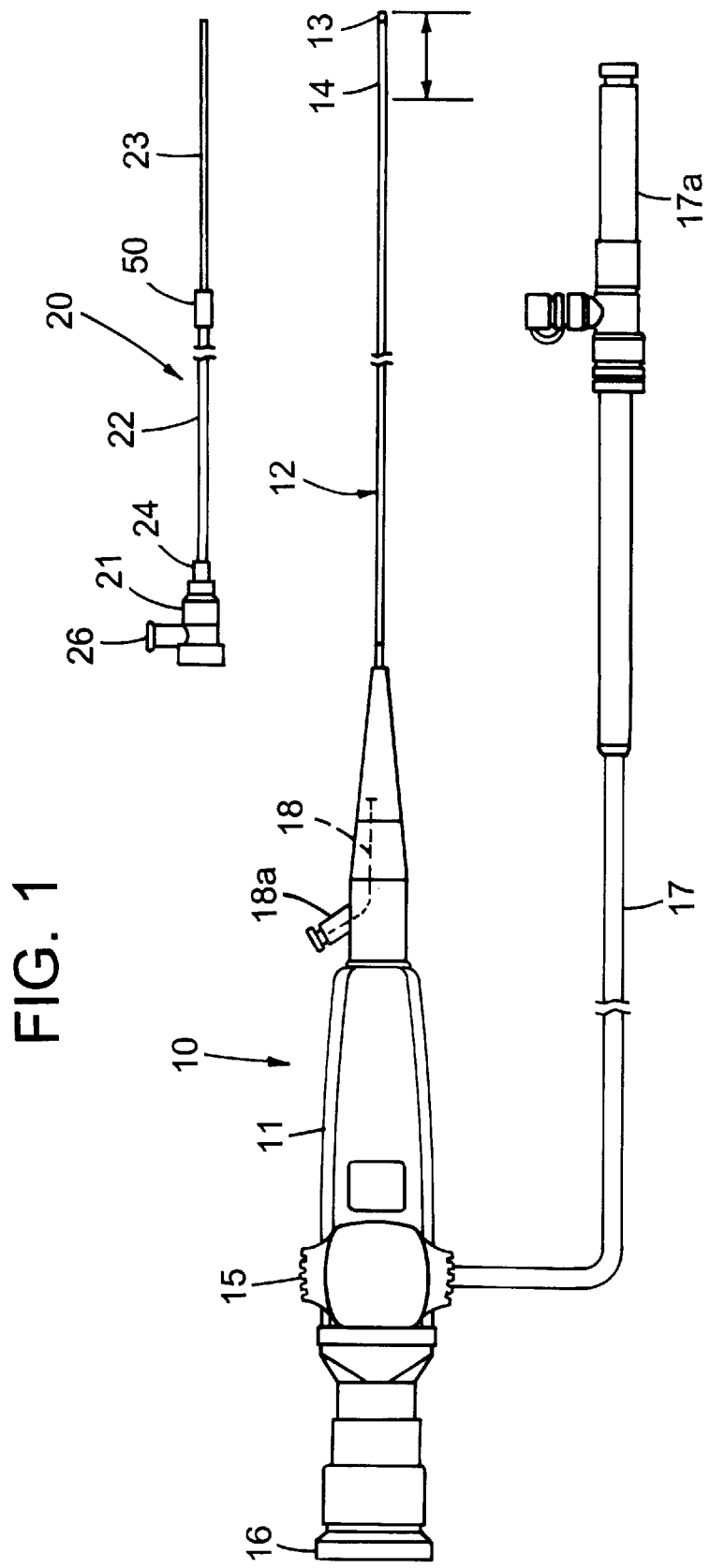
FIG. 1 is a side view of an endoscope unit according to one embodiment of the present invention, in which an endoscope and a fluid supply instrument is illustrated in a separated state.
Figure 2:
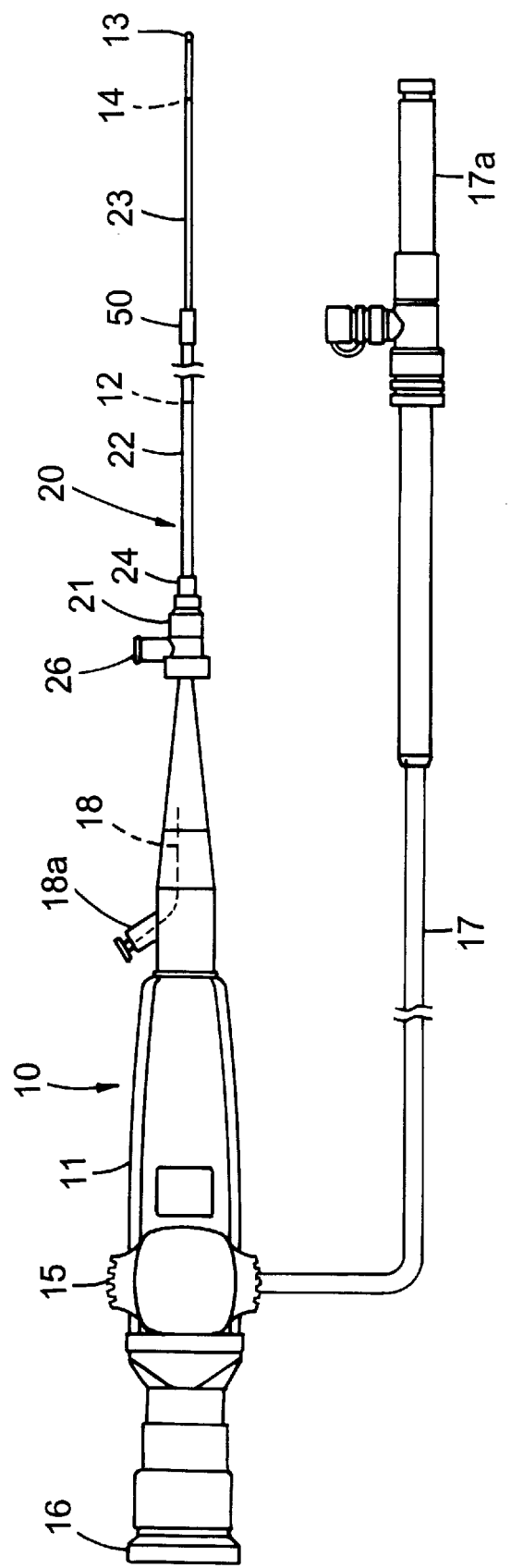
FIG. 2 is a side view of the above endoscope unit in which the fluid supply instrument is attached to the endoscope.

An endoscope unit used for operating the brain of a patient, according to one embodiment of the present invention will now be described with reference to the accompanying drawings. As shown in FIGS. 1 and 2, an endoscope unit includes an endoscope 10 and a fluid supply instrument 20 removably attached to the endoscope 10.

With respect to the endoscope 10, since its construction is almost the same as the ordinary endoscopes, only a brief description is made. The endoscope 10 includes a body 11 and a flexible insertion portion 12 extending from this body 11. The insertion portion 12 is provided at a distal end thereof with a chip 13. An area of the insertion portion 12, which is away by a predetermined length L from a distal end of the insertion portion 12, is a bendable portion 14. A control knob 15 (control member) is provided on the body 11. By turning this control knob 15, the bendable portion 14 is bent through a wire extending through the body 11 and insertion portion 12.

An eyepiece portion 16 is provided on a basal end of the body 11. This eyepiece portion 16 receives an image of an object to be observed through image transmission means including an observation window formed on a distal end face of the chip 13 (distal end face of the insertion portion), an objective lens system, and flux of optical fiber (none of them are shown). A light guide cable 17 extends from a side portion of the body 11. An optical connector 17a is attached to a distal end of this light guide cable 17. Illumination light from a light source (not shown) is supplied to a distal end of the optical connector 17a. This illumination light is supplied to the object to be observed from an illumination window formed on the distal end face of the chip 13 through the flux of optical fiber passing through the optical connector 17a, light guide cable 17, body 11 and the insertion portion 12. The endoscope 10 includes a channel 18 extending through the body 11 and the insertion portion 12. This channel 18 comprises a flexible resin tube (not shown) of a reduced diameter. A basal end of this channel 18 is continuous with an opening of a joint portion 18a disposed at the body 11 and its distal end is continuous with an opening 18b (see FIG. 5) formed in the distal end face of the chip 13.

The fluid supply instrument 20 includes a sleeve-like case 21, a hard pipe 22 extending from a distal end of the case 21 and a thin resilient tube 23 made of resin or the like, extending from a distal end of the hard pipe 22. Here in this embodiment, the hard pipe 22 is about 1.5 to 2 times longer than the resilient tube 23. An inside diameter of the hard pipe 22 is larger than an outside diameter of the insertion portion 12. The resilient tube 23 is flattened in its normal state as a rubber balloon. A peripheral length of the resilient tube 23 is equal to or slightly shorter than a peripheral length of the insertion portion 12.

Figure 3:
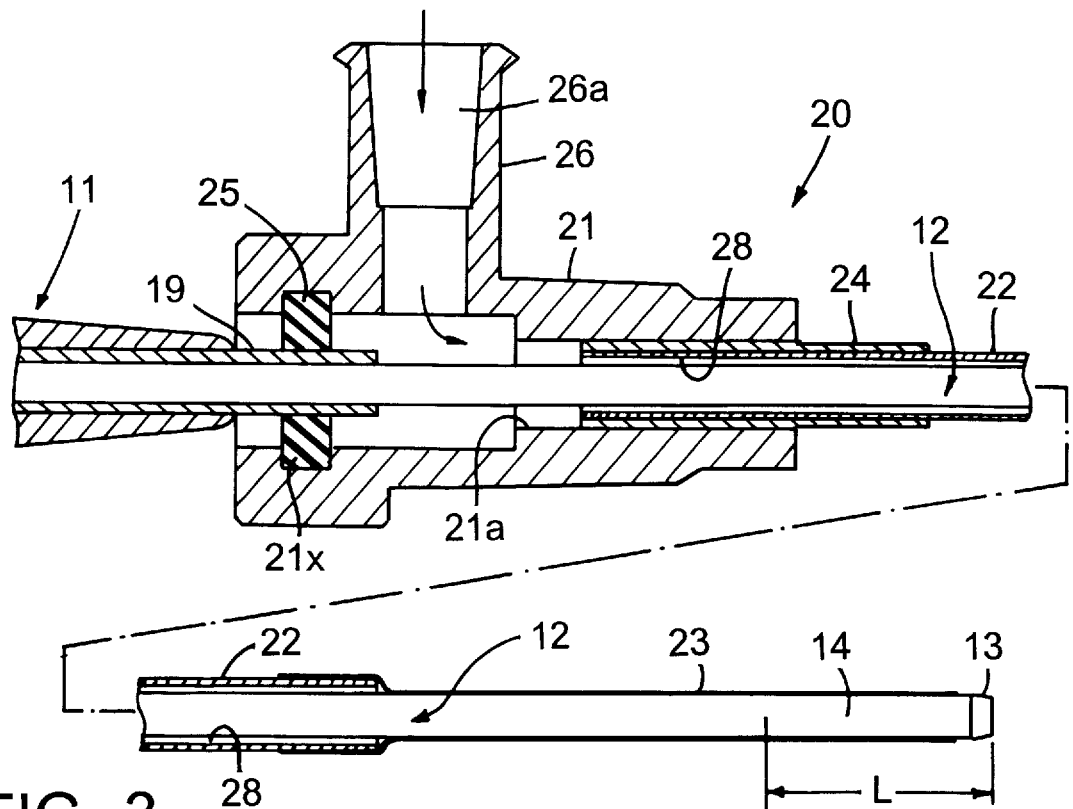
FIG. 3 is an enlarged sectional view of the fluid supply instrument attached to the endoscope.

A construction of the fluid supply instrument 20 is described in more detail. As shown in FIG. 3, the case 21 includes a linearly extending through-hole 21a. A basal end portion of the hard pipe 21 is fixedly inserted into a distal end portion of the through-hole 21a through an auxiliary sleeve 24. An annular groove 21x is formed in an inner periphery of a basal end portion of the through-hole 21a. An annular seal member 25 made of rubber is fitted into this groove 21x. A sleeve-like joint portion 26 perpendicular to the through-hole 21a is formed on a side portion of the case 21. The inside of this joint portion 26 serves as a fluid inlet port 26a. The fluid inlet port 26a is continuous with an intermediate portion of the through-hole 21a.

A basal end of the resilient tube 23 is overlain and attached to an outer periphery of the distal end of the hard pipe 22. The basal end of the resilient tube 23 is secured by winding a thread therearound. A connection portion between the resilient tube 23 and the hard pipe 22 denoted by reference numeral 50 is shown in an exaggerated manner in FIGS. 1 and 2.

The fluid supply instrument 20 thus constructed is removably attached to the endoscope 10 in the following manner. The distal end of the insertion portion 12 is inserted into a rear end opening of the through hole 21a of the case 21 and this case 21 is moved backwardly along the insertion portion 12. Before long, as shown in FIG. 3, the seal member 25 attached to the case 21 is caused to climb over the outer periphery of a reinforcing sleeve 19 extending from the distal end of the body 11 of the endoscope 10. In this way, the resilient tube 23 can easily be attached to the insertion portion 12.

With the attachment of the fluid supply instrument 20, the rear part of the insertion portion 12 of the endoscope 10 is inserted into the hard pipe 22 of the fluid supply instrument 20 with its front part inserted into the resilient tube 23. A small gap 28 is formed between the inner periphery of the hard pipe 22 and the outer periphery of the insertion portion 12. Because the resilient tube 23 is equal to or shorter in peripheral length than the insertion portion 12, it is intimately attached to the outer periphery of the insertion portion 12. The resilient tube 23 covers the insertion portion 12 over its area about two to three times the length of the bendable portion 14 from the distal end of the resilient tube 23. The distal end of the resilient tube 23 is located at the distal end of the insertion portion 12 or nearby area thereof.

Figure 6:
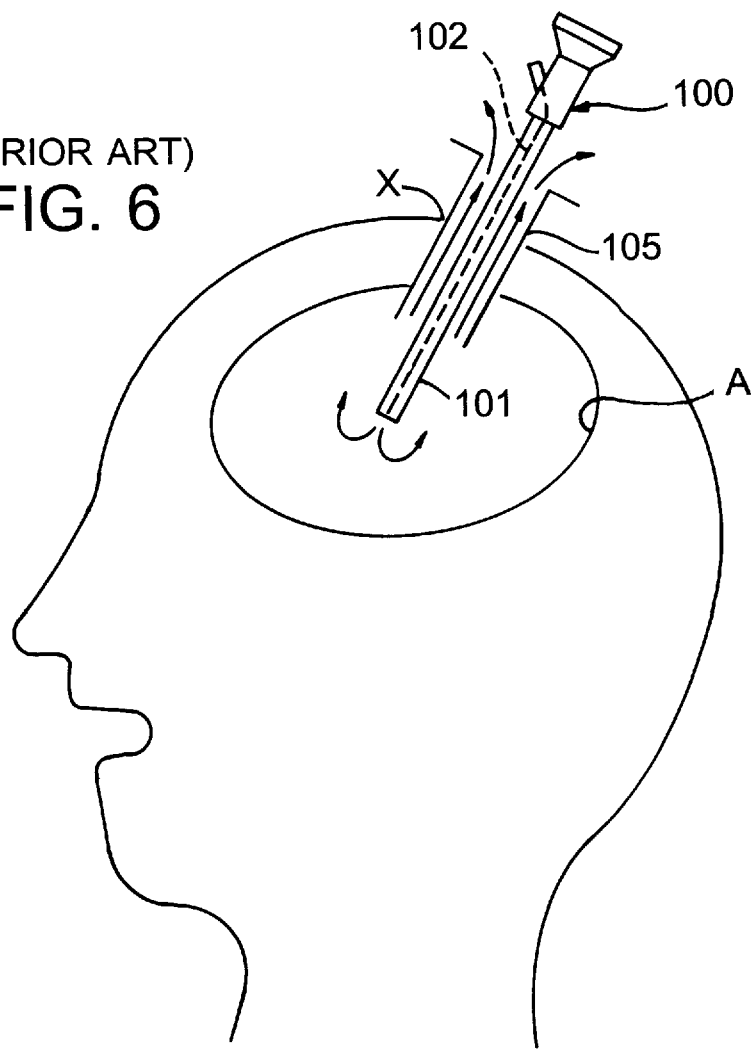
FIG. 6 is a schematic view showing a conventional endoscope unit used for observation and operation of the brain.

The endoscope unit with the fluid supply instrument 20 thus attached to the endoscope 10 is used for operation. That is, a hole is opened in the skull of a patient (see reference numeral X of FIG. 6) and the insertion portion 12 of the endoscope 10 is inserted therein. At that time, the insertion portion 12 is correctly positioned by inserting the distal end portion of the hard pipe 22 of the fluid supply instrument 20 into this hole. For this reason, nevertheless the insertion portion 12 is flexible, it can be introduced to the observation part in the ventricle without useless swaying. Because the gap 28 is easily obtained between the hard pipe 22 and the insertion portion 12 by the hard pipe 22 preliminarily attached to the endoscope 10, the outside diameter of the hard pipe 22 can be reduced compared with the guide tube 105 of the prior art (FIG. 6) in which the guide tube 105 is separately situated from the endoscope 100. For this reason, the hole in the skull can be small and a burden to the patient can be reduced to that extent.

Because the thin resilient tube 23 is intimately contacted with the forward part of the insertion portion 12 as shown in FIGS. 3 and 5, the forward part of the insertion portion 12 is easily pierced deep into the ventricle. The resilient tube 23 does not adversely affect the flexibility of the insertion portion, either. For this reason, the insertion portion 12 can be inserted deep into the ventricle without giving any damage to the brain.

Figure 4:
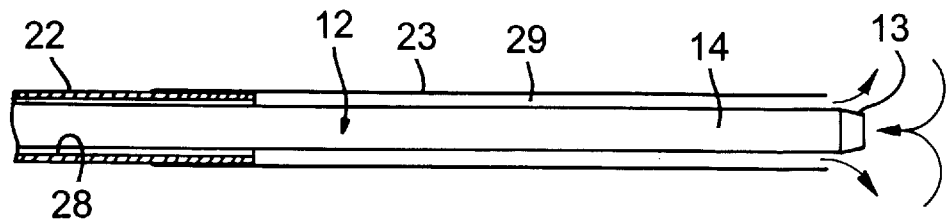
FIG. 4 is an enlarged sectional view of a distal end portion of the fluid supply instrument, in which fluid flows in a resilient tube.
Figures 5A, 5B:
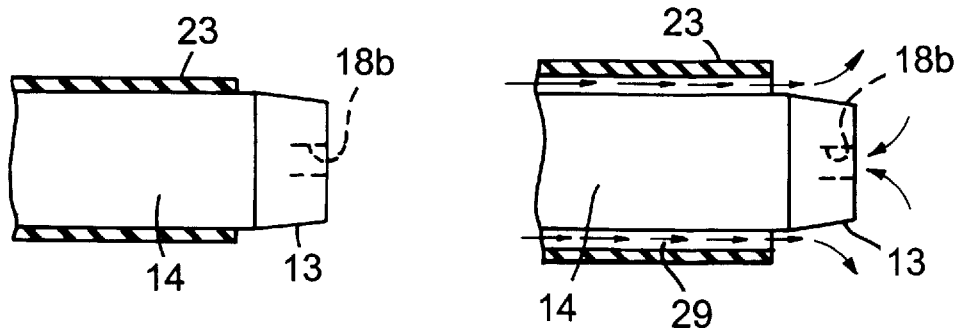
FIG. 5A is an enlarged sectional view showing a relation between a distal end portion of an insertion portion and the resilient tube before fluid is supplied to the resilient tube a thickness of which is shown in an exaggerated manner.
FIG. 5B is a view, similar to FIG. 5A, showing a state when fluid is being supplied.

In case an artificial cerebral spinal fluid is supplied to the ventricle in operation, it is charged into the fluid inlet port 26a of the case 21 from a supply source not shown through a tube. Then, as indicated by arrows of FIG. 3, the artificial cerebral spinal fluid passes through the through-hole 21a of the case 21, then passes through the gap 28 between the hard pipe 22 and the insertion portion 12, and enters between the resilient tube 23 and the insertion portion 12, thereby radially expanding, as shown in FIGS. 4 and 5B, the resilient tube 23 by its fluid pressure. As a consequence, a fluid passage 29 is ensured between the resilient tube 23 and the insertion portion 12. The artificial cerebral spinal fluid flows through this fluid passage 29 so as to be supplied into the ventricle from the distal end of the resilient tube 23. Because the distal end of the resilient tube 23 is arranged in the nearby area of the distal end of the insertion portion 12, a nearby area of the observation window of the chip 13 can be filled with the clean artificial cerebral spinal fluid. As a consequence, a clear observation can be obtained. Further, because the flow sectional area formed between the insertion portion 12 and the resilient tube 23 is large, a sufficient quantity of artificial cerebral fluid can be supplied. This also serves to provide the clear observation. The artificial cerebral fluid is discharged outside from the hole formed in the skull.

Because the seal member 25 is intimately contacted with the outer periphery of the reinforcing sleeve 19, the artificial cerebral fluid is prohibited from leaking backwardly of the case 21 and assuredly supplied to the hard pipe 22 and thus the resilient tube 23.

The surgeon performs an operation to the brain by an elongated forceps (not shown) pierced into the channel 18 while observing the brain through the eyepiece portion 16.

The surgeon can also bend the bendable portion 14 by turning the control knob 15. By doing so, the chip 13 of the endoscope 10 can be brought opposite to a diseased part of the patient. At that time, the resilient tube 23 does not interrupt the bending operation of the bendable portion 14.

After use, the fluid supply instrument 20 can be removed from the endoscope 2 in accordance with necessity. The resilient tube 23 can also be removed from the distal end portion of the hard pipe 22 and discarded.

In case an operation is performed without using the endoscope 10, a suction device may be connected to the joint portion 18a through a tube so that the artificial cerebral spinal fluid in the ventricle can be drawn from the opening 18b through the channel 18. The artificial cerebral spinal fluid may be discharged passing both through the gap between a peripheral edge of the hole formed in the skull and the outer periphery of the hard pipe 22 and through the channel 18 of the endoscope 10. Furthermore, in case the gap between the peripheral edge of the hole in the skull and the outer periphery of the hard pipe 22 is choked, the artificial cerebral spinal fluid may be discharged only through the channel 18.

Although the above endoscope unit is for the use of observation and operation of the brain ventricle, the present invention is not limited to this and can be used for other purposes.

The endoscope may be provided with no channel for passing fluid and the forceps.

The fluid supply instrument may be used for supplying gas such as air.

The insertion portion of the endoscope may be hard.

What is claimed is:

1. An endoscope unit comprising:

an endoscope having an elongated insertion portion; and a fluid supply instrument mounted on the insertion portion, the fluid supply instrument comprising:

a radially expansible, thin, resilient tube receiving the insertion portion and engaging an outer periphery of the insertion portion;

a supply member connected to a basal end of the resilient tube for supplying fluid between the resilient tube and the insertion portion; and a fluid passage formed between an inner periphery of the resilient tube and the outer periphery of the insertion portion when the resilient tube is radially expanded by pressure of the fluid supplied by the supply member.

2. An endoscope unit according to claim 1, wherein a distal end of said resilient tube is located on a distal end of said insertion portion or nearby area thereof.

3. An endoscope unit according to claim 2, wherein a distal end part of the insertion portion is provided as a bendable portion to be remotely controlled, and wherein the resilient tube engages at least an outer periphery of the bendable portion.

4. An endoscope unit comprising:

an endoscope having a flexible, elongated insertion portion; and a fluid supply instrument mounted on the insertion portion, the fluid supply instrument comprising:

a radially expandable, thin, resilient tube receiving a front part of the insertion portion and engaging an outer periphery of the insertion portion;

a linearly extending hard pipe having a distal end connected to a basal end of the resilient tube, the hard pipe being provided with a bore for receiving a rear part of the insertion portion such that a gap is formed between the hard pipe and the insertion portion, and wherein a connection portion between the hard pipe and the resilient tube is located on an intermediate portion of the insertion portion;

a supply member connected to a basal end of the hard pipe for supplying fluid between the resilient tube and the insertion portion; and a fluid passage formed between an inner periphery of the resilient tube and the outer periphery of the insertion portion when the resilient tube is radially expanded by pressure of fluid supplied by the supply member.

5. An endoscope unit according to claim 4, wherein said supply member comprises a hollow case including a through-hole for allowing said insertion portion to be pierced therein and a fluid inlet port continuous with the intermediate portion of said through-hole, and an annular seal member for sealing between an inner periphery of a rear end portion of said through-hole and an outer periphery of said insertion portion, the basal end of said hard pipe being fixedly inserted into a distal end portion of said through-hole.

* * * * *